United States Patent [19]
Kranzler et al.

[11] Patent Number: 5,641,566
[45] Date of Patent: Jun. 24, 1997

[54] HIGH STRENGTH POROUS PTFE SHEET MATERIAL

[75] Inventors: Thane L. Kranzler; Jon P. Moseley, both of Flagstaff, Ariz.

[73] Assignee: W. L. Gore & Associates, Inc., Newark, Del.

[21] Appl. No.: 569,419

[22] Filed: Dec. 6, 1995

Related U.S. Application Data

[62] Division of Ser. No. 281,396, Jul. 27, 1994, abandoned.

[51] Int. Cl.$^6$ .............................. B32B 7/00; A61B 17/00
[52] U.S. Cl. ...................... 428/315.7; 428/304.4; 428/308.4; 428/315.5; 428/315.9; 600/37
[58] Field of Search ........................ 428/304.4, 316.6, 428/220, 913, 308.4, 315.5, 315.7, 315.9; 623/1, 11; 606/151; 602/47; 600/37

[56] References Cited

U.S. PATENT DOCUMENTS

| | | |
|---|---|---|
| 3,953,566 | 4/1976 | Gore . |
| 4,187,390 | 2/1980 | Gore . |
| 4,277,429 | 7/1981 | Okita . |
| 4,385,093 | 5/1983 | Hubis . |
| 4,478,665 | 10/1984 | Hubis . |
| 4,482,516 | 11/1984 | Bowman et al. . |
| 4,598,011 | 7/1986 | Bowman . |
| 4,671,754 | 6/1987 | Okita et al. . |
| 5,100,422 | 3/1992 | Berguer et al. . |
| 5,290,217 | 3/1994 | Campos . |
| 5,321,109 | 6/1994 | Bosse et al. . |
| 5,433,996 | 7/1995 | Kranzler et al. . |

FOREIGN PATENT DOCUMENTS 9413224  6/1994  WIPO .

*Primary Examiner*—Kathleen Choi
*Attorney, Agent, or Firm*—Wayne D. House

[57] ABSTRACT

A high strength, porous PTFE sheet material having high strength in all directions within the plane of the sheet material. The sheet material has, within the plane of the sheet, a higher minimum tensile strength, matrix tensile strength, secant modulus and matrix secant modulus than previously known porous PTFE sheet materials. The sheet material is a laminate of multiple layers of porous PTFE film, preferably uniaxially expanded film, wherein the orientation of the direction of the fibrils of any layer varies slightly, such as about ten degrees, from the orientation of the fibrils of the adjacent layer. The sheet material is particularly useful as a surgical repair patch and especially as a blood vessel repair patch because of its high strength, flexibility, biocompatibility and very low rate of suture line bleeding.

9 Claims, 3 Drawing Sheets

HIGH STRENGTH POROUS PTFE SHEET MATERIAL

This application is a division of application Ser. No. 08/281,396, filed Jul. 27, 1994 abandoned and refiled as Ser. No. 08/625,785 on Mar. 29, 1996, now allowed.

FIELD OF THE INVENTION

This invention relates to high strength, porous polytetrafluoroethylene sheet materials and to tubes made from such materials.

BACKGROUND OF THE INVENTION

Porous polytetrafluoroethylene (hereinafter PTFE), made by expansion by stretching at a temperature below the crystalline melt temperature of porous PTFE, has been known for some time. These porous, fibrillated materials and their manufacture were originally described by Gore in U.S. Pat. Nos. 3,953,566 and 4,187,390. They possessed the known attributes of PTFE while adding additional benefits resulting from their porous microstructure. They are typically hydrophobic, inert, strong and can be made to be thin and flexible. Applications for these materials include wire insulation, gaskets, waterproof and breathable rainwear and various surgically implantable medical devices such as vascular grafts, surgical repair patches, sutures and periodontal repair materials.

The greatest strength of these materials is typically in the direction in which they were expanded by stretching, the same direction in which the fibrils of the porous microstructure are oriented. Thus uniaxially expanded materials are predominantly strong in the single direction in which they were expanded.

Multiaxially expanded porous PTFE sheet materials are known, such as GORE-TEX® Soft Tissue Patch and GORE-TEX® Cardiovascular Patch (W. L. Gore & Associates, Inc., Flagstaff, Ariz.). These materials are implantable surgical repair patch materials which have fibrils oriented in virtually all directions within the plane of the sheet and substantially equal strength in all directions within the plane of the sheet. The strongest presently available porous PTFE sheet material is believed to be GORE-TEX® Cardiovascular Patch which has a mean tensile strength of about 29.8 megapascals, a mean matrix tensile strength of 133.6 megapascals, a mean secant modulus of 46.8 megapascals, and a mean matrix secant modulus of 209.8 megapascals, with all data taken from randomly selected directions within the plane of the material.

Other references which teach the manufacture of porous PTFE sheet materials include U.S. Pat. No. 4,482,516 to Bowman et al., which describes a biaxially stretched film, and U.S. Pat. Nos. 4,385,093 and 4,478,665 to Hubis which teach a method of making laminated, porous PTFE sheet materials having good bond strengths between the adjacent layers.

SUMMARY OF THE INVENTION

The present invention is a high strength, porous PTFE sheet material having a higher minimum tensile strength within the plane of the sheet material than any previously known porous PTFE sheet material. The inventive sheet material also has a higher minimum matrix tensile strength, secant modulus and matrix secant modulus than previously known porous PTFE sheet materials. Matrix strength values compensate for the porosity of the material. The sheet material also has excellent creep resistance in all directions within the plane of the sheet.

The inventive sheet materials have high strength in substantially all directions in the plane of the film. When describing the inventive material as having higher minimum strengths than previously known porous PTFE sheet materials, it is meant that the strength of the inventive material measured in the direction within the plane of the material that yielded the lowest strength value would be considerably greater than the same strength measurement of previous porous PTFE sheet materials.

A preferred way to determine the minimum strength value for a sheet of porous PTFE material is to cut a rectangular sample of 7.62 cm by 1.27 cm from the material with the length of the sample in a randomly selected direction. A second rectangular sample is then cut from another area of the same sheet with the length of the second sample oriented perpendicular to that of the first. Additional samples oriented in different directions from the first two samples may also be measured if desired. The sample strengths are then measured substantially according to Test Method A of ASTM D882-91, with the weakest strength of the measured samples being the determining value. Test methodology will be further described including test sample dimensions and strain rate. If it is necessary to test smaller samples than those described herein, then the length and width of the test sample should both be reduced proportionately while still using the specified strain rate.

The material of the present invention is anticipated to be useful as an implantable surgical repair patch and particularly useful as a blood vessel repair patch material. Its high strength, flexibility and biocompatibility are all desirable for these applications. Surprisingly, especially in view of the thin wall thickness possible with the inventive material as a strong blood vessel repair patch, the material is more resistant to suture line bleeding immediately after implantation than previously known patch materials consisting essentially of porous PTFE.

The porous PTFE sheet material of the present invention is made by laminating together multiple layers of porous PTFE film, the film having been made by expansion by stretching resulting in a porous, fibrillar microstructure. Films of this type are made as taught by U.S. Pat. No. 4,187,390 to Gore, incorporated by reference herein. Preferred films are uniaxially expanded films which are quite strong in the direction in which they were expanded, the same direction in which the fibrils of the porous, fibrillar microstructure are oriented. These uniaxially expanded films, however, have less strength in directions within the plane of the film other than the direction in which they were expanded. Their strength in the direction perpendicular to the direction of expansion is typically much less than the strength measured in the direction of expansion. The inventive sheet material is made by laminating together multiple layers of these uniaxially expanded films, wherein the various layers of the laminated film have the direction of fibrillar orientation in various different directions. For the resulting laminated sheet material to have substantially equal strength when tested in any randomly selected direction within the plane of the sheet material, the various layers of the laminate are preferably laid up with a substantially equal amount of angular deviation of the fibrillar orientation between adjacent layers. For example, 18 layers of film can be used to make the sheet material with the adjacent layers of film laid up with their fibrillar orientations about ten degrees apart. Furthermore, it has been found that the adhesion of adjacent layers of film is substantially improved if the angular deviation of the fibrillar orientations of adjacent film layers is relatively slight, such as about ten degrees.

It is apparent that it is possible to tailor directional strength characteristics of porous sheet materials by variations of the above construction process wherein porous PTFE films are laminated together to produce both relative strength and weakness in different desired directions.

It is anticipated that biaxially expanded films may also be laminated together to produce the inventive sheet material, however, it is believed that a lamination of biaxial films will not result in a sheet material as strong as one made by the previously described process of laminating uniaxially expanded films. This is because uniaxial films typically have a much greater maximum strength in the direction of expansion than the maximum strength of presently known biaxial films.

Peel testing on laminated film layers with fibrillar orientations differing in increments of 5 degrees, from a difference in orientation between adjacent layers ranging from zero degrees up to ninety degrees, indicates that a difference of twenty degrees results in a noticeably weaker bond between adjacent layers than angles of zero to 15 degrees. A difference of 90 degrees produced the weakest bond.

The adjacent layers are preferably bonded together with pressure and heat above the crystalline melt temperature of the PTFE, typically above about 327° C. In this manner a multi-directionally strong sheet material of porous expanded PTFE can be made without the use of non-PTFE adhesives.

Alternatively, an adhesive may be used between the layers of PTFE film to adhere adjacent layers together. The PTFE film may be made with the adhesive on only one surface of the film. The adhesive coated films are oriented during tacking of the film layers so that the adhesive-coated side of one film layer contacts the uncoated PTFE side of the adjacent film layer. The adhesive is preferably in the form of a discontinuous, porous coating in order to have a minimal effect on the porosity of the completed sheet material. Conversely, a continuous, non-porous adhesive coating may be used if a non-porous sheet material is intended. The adhesive must be biocompatible for implantable, medical device applications; preferred adhesives are thermoplastics of lower melt point than the crystalline melt point of the PTFE film. Thermoplastic fluoropolymers such as fluorinated ethylene propylene (hereinafter FEP) are most preferred. These types of adhesives are activated by placing the adhesive-coated porous PTFE sheet material into an oven at a combination of time and temperature adequate to cause melting of the adhesive.

The FEP-coated porous PTFE film is made by a process which comprises the steps of:

a) contacting a porous PTFE substrate, usually in the form of a membrane or film, with another layer which is preferably a film of FEP or alternatively of another thermoplastic polymer;

b) heating the composition obtained in step a) to a temperature above the melting point of the thermoplastic polymer;

c) stretching the heated composition of step b) while maintaining the temperature above the melting point of the thermoplastic polymer; and d) cooling the product of step c).

In addition to FEP, other thermoplastic polymers including thermoplastic fluoropolymers may also be used to make this coated film. The adhesive coating on the porous PTFE film may be either continuous (non-porous) or discontinuous (porous) depending primarily on the amount and rate of stretching, the temperature during stretching and the thickness of the adhesive prior to stretching.

Tubular embodiments of the inventive sheet material are also possible. The sheet material may be rolled into the form of a tube whereby the tube has a seam of overlapping edges of the sheet material. Alternatively, a tube may be fabricated from layers of film wherein adjacent layers of uniaxially expanded film are wrapped around a mandrel with the fibrillar orientation of the adjacent layers varying by a slight angular amount. For example, the inner layer of film may have a fibrillar orientation parallel to the longitudinal axis of the tube, the next layer may deviate by a small amount such as ten degrees and so on, until the outer layer has an orientation that is close to being circumferential or perpendicular to the longitudinal axis of the tube. The mandrel may be removed after lamination of the adjacent film layers. In this fashion a strong, flexible tube of porous PTFE film may be made.

In an alternative tubular embodiment, the above described layers of film may be applied to the outer surface of a uniaxially expanded tube of porous PTFE. Such a tube may be made according to the teachings of U.S. Pat. No. 4,187,390.

DETAILED DESCRIPTION OF THE INVENTION

Figure 1:
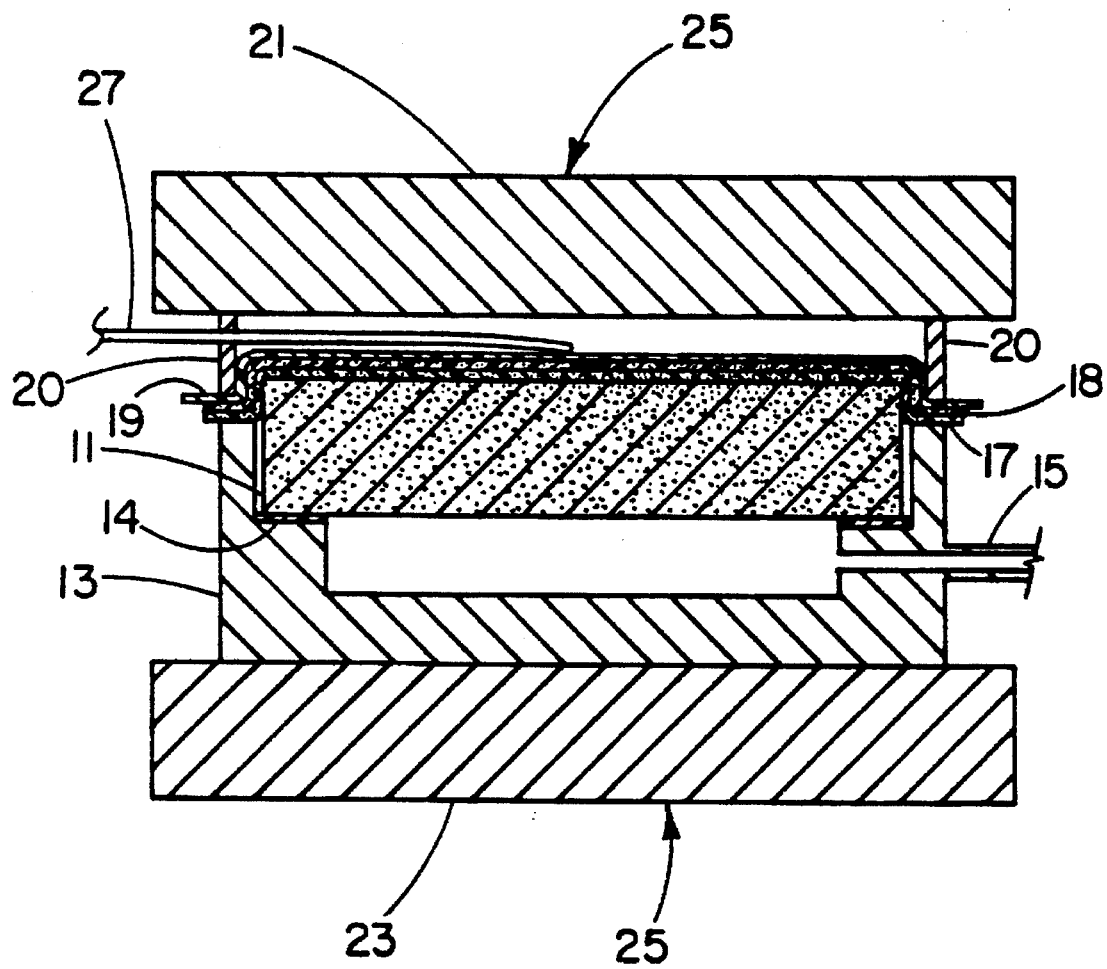
FIG. 1 describes a cross sectional view of an apparatus useful for laminating porous PTFE films to make the inventive sheet material.

The preferred method of making the laminated, porous PTFE sheet material involves stacking individual layers of porous PTFE film over the flat surface of a porous metal plate to which a vacuum has been applied. The laminating apparatus is described by FIG. 1. To construct samples of the sheet material, a vacuum was applied to fixture 13 via port 15. Fixture 13 supports porous metal plate 11 sealed by a gasket 14. The porous metal plate (316L stainless steel, approximately 5 micron pore size, Mott Metallurgical Corp., Farmington Conn., part no. 10005-6.5-.5), had a 15 cm diameter circular surface and was of about 1 cm thickness. A sheet of porous, PTFE film 17 having a uniaxial fibrillar orientation was placed over the surface of the porous metal plate 11 so that there were essentially no wrinkles in the film 17, with the vacuum below the porous metal plate 11 holding the film 17 in place. The film used was of about 0.01 mm thickness, about 16.5 cm width and 20 cm length, and had a density of about 0.3 g/cc and a fibril length of about 50 microns. This fibril length is an estimated mean value determined by examining scanning electron photomicrographs of the film surface. The density of solid, non-porous PTFE is generally considered to be about 2.2 g/cc, consequently the film used was about 86% porous by bulk volume. A second layer 18 of the same film was placed over the first layer 17, with the fibrillar orientation of the second layer 18 rotated ten degrees with respect to the fibrillet orientation of the first layer 17. A third layer was then placed over the second, rotated an additional ten degrees. This procedure continued until 18 layers had been stacked together with an equal angular deviation of the fibrillet orientation provided between adjacent film layers. The third and subsequent layers of film have been omitted from the FIG. 1 for clarity. Sheet materials made by this method were thus made in multiples of 18 layers.

After the desired number of layers of film had been provided as described in multiples of 18 layers, a sheet of polyimide film 19 (Kapton®, DuPont de Nemours, Circleview, Ohio) of about 0.05 mm thickness and of larger length and width than the porous PTFE film sheets, was placed over the stack of film sheets. A circular steel restraining ring 20 was placed over the edges of the polyimide film-covered stack of porous PTFE film. The inside diameter of the retaining ring 20 was of larger diameter than the diameter of the porous metal plate 11 so that only a slight amount of interference existed when even 72 layers of porous PTFE film were used in the stack. A compressive force 25 of about 450 kg was applied to the ring by a Carver laboratory press (model M, Fred Carver Inc., Menomonee Falls, Wis.). The force 25 was applied via heavy metal plates 21 and 23 heated by electrical cartridge heaters. The temperature of the surface of the polyimide film 19 was monitored by a thermocouple 27 connected to an electronic temperature controller; thirty minutes after reaching an indicated temperature of 365° C., the heated press with metal plates 21 and 23 was removed and the stack of film layers was allowed to cool. The covering sheet of polyimide film 19 was then removed from the laminated stack of porous PTFE film layers.

Various samples of the high strength porous PTFE sheet material made according to this method were subjected to mechanical tests intended to measure tensile strength and matrix tensile strength, secant modulus and matrix secant modulus, suture retention strength and suture hole water leakage. The thickness of the samples varied with the different samples having been made from 18, 36, 54 and 72 layers of the previously described film. The typical finished thicknesses of these four different thickness samples were, respectively, 0.07 mm, 0.14 mm, 0.21 mm and 0.28 mm. Except for the suture hole water leakage test, all tests were performed using 72 layer inventive samples. Some data were normalized to compensate for the different thicknesses of the inventive and control samples. Samples of GORE-TEX Cardiovascular Patch were used as controls for all tests. Mechanical tests were performed in randomly selected directions within the plane of the sheet material samples.

Tensile testing was carried out on an Interlaken servohydraulic machine (model no. 3300 test frame with a model no. 3200 controller; Interlaken Technology Corporation, Eden Prairie, Minn.) operating under displacement control at constant speed. Testing was performed according to Test Method A of ASTM Standard D882-91 except that the same gauge length was used for the determination of all data for both control and inventive samples, as opposed to the longer gauge length specified by ASTM for the modulus testing samples. This was necessary due to the limited size of the sheets from which the test samples were cut. All samples were cut to a length of 7.62 cm and a width of 1.27 cm. The thickness of each cut sample was determined to be the mean of three measurements made using a Starrett model no. 1015MB-881 snap gauge (Starrett Corp., Athol, Mass.) at three different locations within the length of the sample. The gauge length after allowing for sample grip length was 3.81 cm; model no. 2712-003 Instron pneumatic grips (Inetton Corporation, Canton, Mass.) were used for all testing at an operating pressure of 590 kilopascals. Serrated grip faces (Instron Model No. 2702-016) were used for all testing except for determination of tensile strength for the GORE-TEX Cardiovascular Patch material which required the use of rubber-coated grip faces (Instron Model No. 2702-015) in order to prevent grip breaks in this material. Additionally, it was found necessary to provide the inventive samples with gripping tabs in order to prevent the samples from slipping out of the serrated grips during testing. Tabs were also added to the GORE-TEX Cardiovascular Patch modulus testing specimens in order to provide comparable data. The tabs were made by cutting a rectangular strip of 0.4 mm thick GORE-TEX Cardiovascular Patch to a 3.81 cm length and 1.27 cm width, folding the strip in half across its width and bonding the folded strip to the end of the test specimen with cyanoacrylate cement so that the end edge of the test specimen contacted the fold of the tab. In this manner, a 1.9 cm length of the end of each sample was covered by the tab material. The entire tab-covered surface of the test specimen was in contact with the opposing grip surfaces during testing, leaving the test specimen with a 3.81 cm gauge length.

Testing was performed at a rate of 6.35 mm/sec resulting in a strain rate of 1000% per minute. From the resulting plot of force vs. displacement provided by the testing machine and from measurements of sample thickness, width and gauge length, values were determined for tensile strength and secant modulus. Secant modulus was determined at 25 percent of mean tensile strength; the zero point on the strain axis was determined as described by ASTM D638-91, section A1.3 for material with no Hookean region. For the inventive material, secant modulus was determined at 24.37 megapascals; for 0.4 mm GORE-TEX Cardiovascular Patch, secant modulus was determined at 7.45 megapascals. Results are presented in Table 1; all units are megapascals.

TABLE 1

| MATERIAL | TENSILE STRENGTH | STD. DEV. | SAMPLE SIZE | SECANT MODULUS | STD. DEV. | SAMPLE SIZE |
| --- | --- | --- | --- | --- | --- | --- |
| Inventive Sheet | 97.5 | 2.93 | 8 | 537.4 | 29.1 | 6 |
| .4 mm GORE-TEX Cardiovascular Patch | 29.8 | 2.84 | 15 | 46.8 | 3.08 | 7 |

Because the inventive and control samples are porous materials, tensile strength values were converted to matrix tensile strength values in order to compensate for differing degrees of porosity. The GORE-TEX Cardiovascular Patch material was typically about 78% porous while the inventive sheet materials were typically about 55% porous. Matrix tensile strength was obtained by multiplying the tensile strength of each individual sample, determined as described above, by the ratio of the 2.2 g/cm$^3$ density of solid, non-porous PTFE to the density of the porous sample. Density was determined by cutting at least five round samples of 2.54 cm diameter from the same sheet from which the tensile sample had been cut. The thickness of each of these samples was measured as described above; all samples were weighed together on a Mettler model no. AE100 analytical balance (Mettler Instrument Corporation, Hightstown, N.J.). The density was then calculated from the total weight of all the samples with respect to the total volume of the samples as based on the average thickness and total area of all the samples. Mean density of the inventive samples was 0.995 g/cm$^3$; mean density of the GORE-TEX Cardiovascular Patch was 0.491 g/cm$^3$.

Matrix secant modulus was obtained by multiplying the secant modulus of each individual sample, determined as described above, by the ratio of the density of solid, non-porous PTFE to the density of the porous sample. Matrix tensile strength and matrix secant modulus results for the same samples described in Table 1 are presented in Table 1A; all units are megapascals.

TABLE 1A

| MATERIAL | MATRIX TENSILE STRENGTH | STD. DEV. | MATRIX SECANT MODULUS | STD. DEV. |
| --- | --- | --- | --- | --- |
| Inventive Sheet | 215.6 | 6.48 | 1,188.1 | 64.3 |
| .4 mm GORE-TEX Cardiovascular Pitch | 133.6 | 12.73 | 209.8 | 13.81 |

Figure 2:
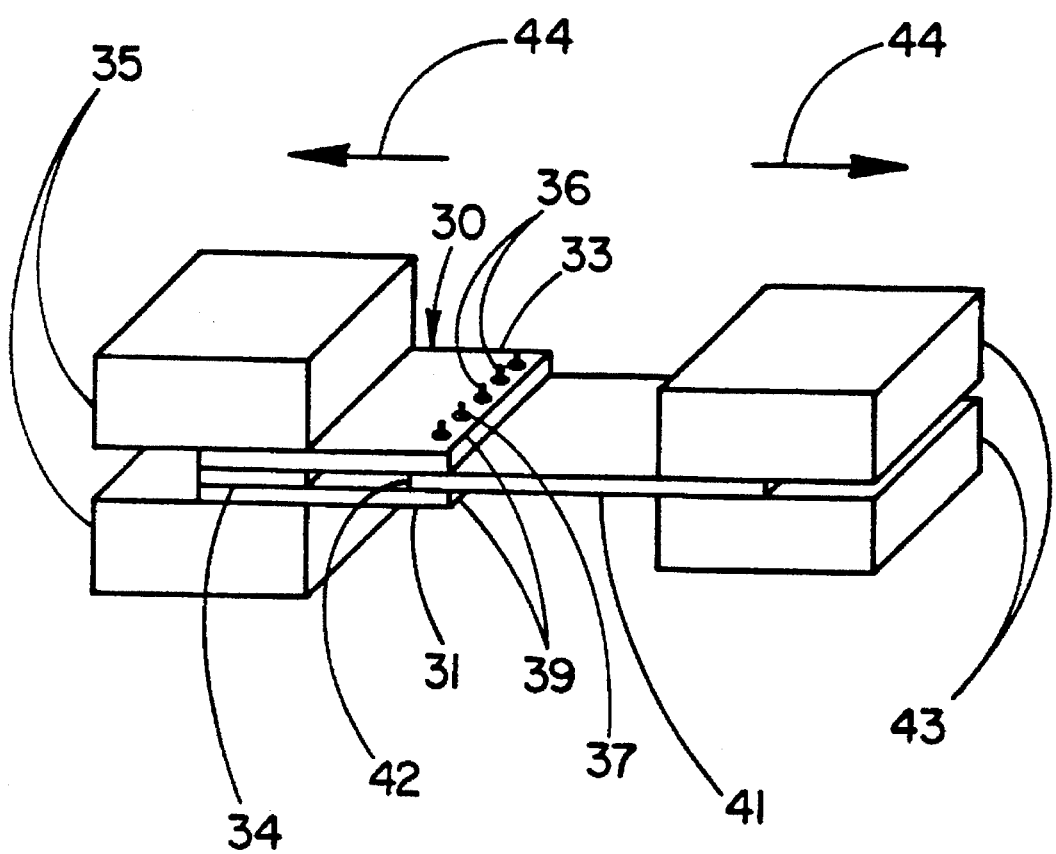
FIG. 2 describes an apparatus for measuring the suture retention capability of the sheet material.

The suture retention capability of the inventive material was measured using a fixture designed to simulate the forces applied by a line of sutures as shown by FIG. 2. The fixture 30 consisted of two plates 31 and 33 held between tester grips 35 and separated by a spacer plate 34. Plate 31 had five pointed, steel pins 36 of 0.5 mm diameter arranged in a straight line and spaced 2 mm apart on centers. These pins were pushed through a sample of test material 41 adjacent to an edge 42 of the material so that the line of pins 36 was parallel to the material edge 42 and located 4 mm from that edge 42 with respect to the pin centers. Pins 36 then fit through five correspondingly spaced holes 37 in the second plate 33 for additional support of the pins during the test. The fixture 30 was placed into one of the grips 35 of the Interlaken testing machine while the other end of the test material 41 opposite the edge 42 pierced by the five pins 36 was placed into the other grips 43 of the testing machine. In this manner all five pins 36 were pulled toward the adjacent edge 42 of the material sample 41 as indicated by arrows 44. The material was pulled at a fixed rate of either a high rate of 89 cm/sec or a low rate of 20 cm/min until the pins pulled through the edge 42 of the material. The force value at which this failure occurred was then recorded by the testing machine. Comparison data were provided by testing both GORE-TEX Cardiovascular Patch and GORE-TEX Soft Tissue Patch. Six samples of each type were tested. The resulting data are summarized in Table 2.

TABLE 2

| MATERIAL | LOW RATE, newtons | STD. DEV. | NORMAL- IZED, N/mm | HIGH RATE, newtons | STD. DEV. | NORMAL- IZED, N/mm |
| --- | --- | --- | --- | --- | --- | --- |
| .28 mm Thick Film Laminate | 189 | 34.3 | 675 | 83.6 | 6.4 | 298 |
| 0.4 mm GORE-TEX Cardiovascular Patch | 68 | 5.7 | 170 | 14.2 | 0.84 | 35.5 |
| 1.0 mm Thick GORE-TEX Soft Tissue Patch | 89.1 | 2.6 | 89.5 | 114.2 | 21.1 | 114.2 |

Figure 3:
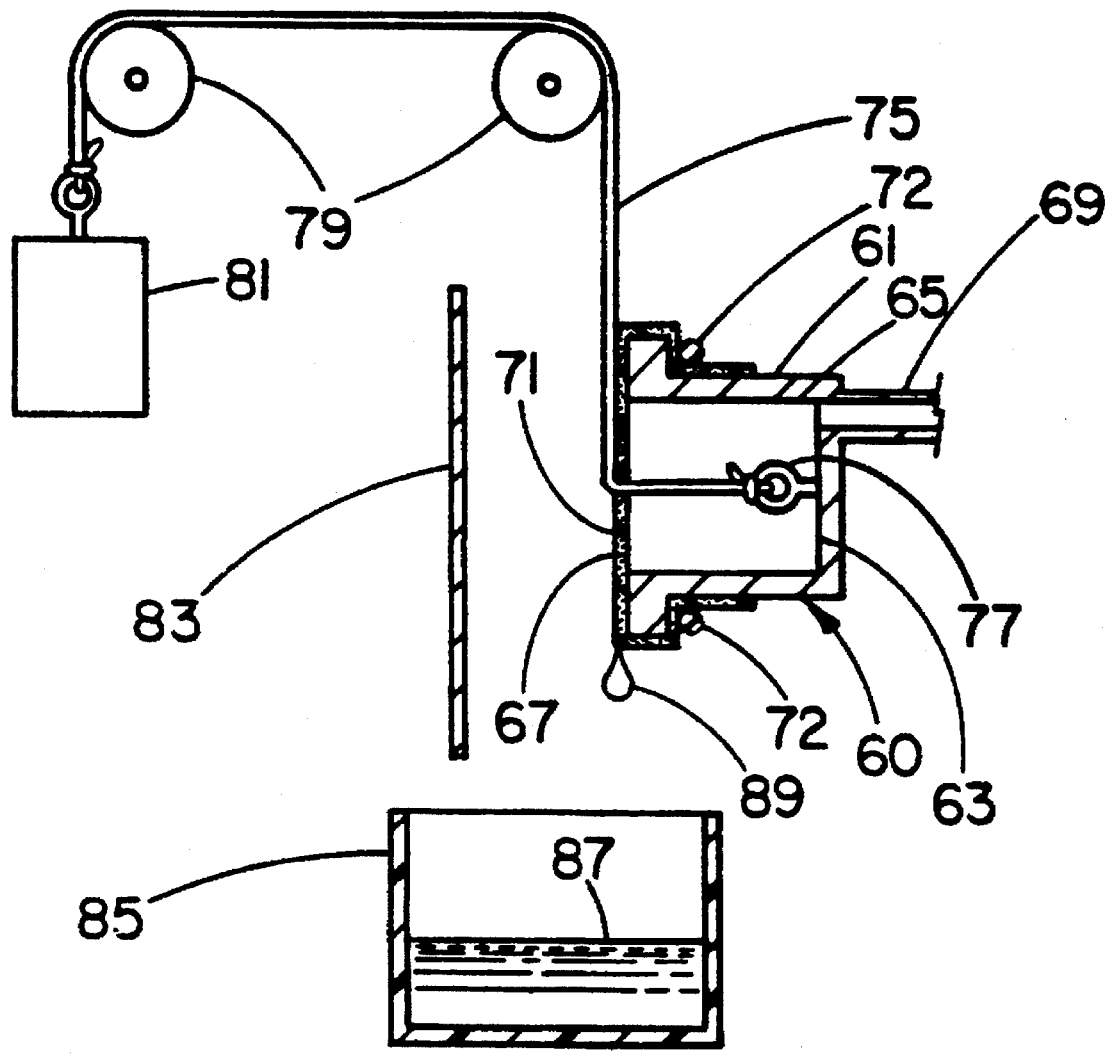
FIG. 3 describes a cross sectional view of an apparatus for measuring water leakage through a suture hole through the thickness of a sheet material of the present invention.

A simple in-vitro test was developed to allow screening of sheet materials for suture hole bleeding. As shown by FIG. 3, the test machine 60 consisted of a housing 61 containing a chamber 65 with an open side 67 of about 2.54 cm diameter over which a sample 71 of sheet material to be tested was secured in a water-tight manner by a clamping fixture 72. Smaller chamber sizes may be used for smaller size samples. The open side 67 of the machine 60 was vertically-oriented as was the portion of the sample 71 to be tested. A 6-0 stainless steel suture 75, attached to an anchor 77 inside the machine 60, was passed through a hole previously created in the center of the sample 71 by piercing the sample with a 0.34 mm diameter steel pin having a tapered point. The suture 75 was then routed up and over two pulleys 79. After the sample 71 of sheet material was secured to the test machine 60, deionized water at 40° C. introduced into the chamber 65 via port 69 and circulated for approximately one minute in order to bring the sample 71 up to the same temperature. A 100 g weight 81 was then attached to the suture 75 and the chamber 65 was simultaneously pressurized to 26 kilopascals. Water 87 and 89 leaking out of the suture hole was directed into a graduated cylinder 85 and collected for a period of one minute; any water squirting from the suture hole was diverted by baffle 83 into the graduated cylinder 85. The process was repeated on 10 samples per patch, and a two-sample Student's t test was used to compare the leakage rates between the different materials. The data are described in Table 3. Briefly, the GORE-TEX Cardiovascular Patch samples leaked on average 10.7 ml/min. while the inventive samples leaked on average less than that amount. The 36 layer inventive samples leaked an average of 8.2 ml/min. while the 72 layer inventive samples leaked an average of 5.8 ml/min. Patch materials have not been heretofore available which leaked on average less than 6.0 ml/min, or likewise less than 8.2 ml/min.

TABLE 3

| MATERIAL | LEAKAGE ml/min WITH STEEL SUTURE | STANDARD DEVIATION |
| --- | --- | --- |
| 36 LAYER | 8.2 | 2.0 |
| 72 LAYER | 5.8 | 2.5 |
| 0.6 mm GORE-TEX CARDIOVASCULAR PATCH | 10.7 | 1.6 |

We claim:

1. A surgical repair patch consisting essentially of layers of porous polytetrafluoroethylene film laminated together to form a planar sheet of porous polytetrafluoroethylene having a thickness of less than about 0.6 mm, wherein said planar sheet leaks less than 8.2 ml/min of water when tested with a 6-0 steel suture at a water pressure of 26 kilopascals and at a temperature of about 40° C.

2. A surgical repair patch according to claim 1 wherein the planar sheet leaks less than 6.0 ml/min of water.

3. A surgical repair patch according to claim 2 wherein the planar sheet has a thickness of less than about 0.4 mm.

4. A surgical repair patch according to claim 2 wherein the planar sheet has a thickness of less than about 0.3 mm.

5. A surgical repair patch according to claim 1 wherein the planar sheet has a thickness of less than about 0.4 mm.

6. A surgical repair patch according to claim 1 wherein the planar sheet has a thickness of less than about 0.3 mm.

7. A surgical repair patch consisting essentially of layers of porous polytetrafluoroethylene film laminated together to form a planar sheet of porous polytetrafluoroethylene having a thickness of less than about 0.6 mm, wherein said planar sheet leaks less than an average of 10.7 ml/min of water when tested with a 6-0 steel suture at a water pressure of 26 kilopascals and at a temperature of about 40° C.

8. A surgical repair patch according to claim 7 wherein the planar sheet has a thickness of less than about 0.4 mm.

9. A surgical repair patch according to claim 7 wherein the planar sheet has a thickness of less than about 0.3 mm.

\* \* \* \* \*